(12) United States Patent
Philbrook

(10) Patent No.: US 7,238,532 B1
(45) Date of Patent: Jul. 3, 2007

(54) ISOTHIAZOLONE MONITORING IN AQUEOUS SYSTEMS

(76) Inventor: David Michael Philbrook, 3412 Yelverton Cir., Raleigh, NC (US) 27612

( * ) Notice: Subject to any disclaimer, the term of this patent is extended or adjusted under 35 U.S.C. 154(b) by 643 days.

(21) Appl. No.: 10/158,910

(22) Filed: Jun. 3, 2002

Related U.S. Application Data

(60) Provisional application No. 60/294,556, filed on Jun. 1, 2001.

(51) Int. Cl.
*G01N 33/00* (2006.01)

(52) U.S. Cl. .................. 436/92; 436/174; 436/175; 436/177; 436/178

(58) Field of Classification Search .............. 436/92, 436/177
See application file for complete search history.

(56) References Cited

U.S. PATENT DOCUMENTS

| | | | |
|---|---|---|---|
| 3,975,155 A | | 8/1976 | Geyer |
| 4,110,378 A | | 8/1978 | Geyer |
| 4,652,530 A | * | 3/1987 | Rothman et al. .............. 436/92 |
| 4,787,972 A | * | 11/1988 | Stubblebine ................. 210/196 |
| 5,094,957 A | * | 3/1992 | Willingham ................. 436/92 |
| 6,375,856 B1 | * | 4/2002 | Seshimoto et al. ......... 210/791 |
| 6,541,228 B1 | * | 4/2003 | Genders et al. ............. 435/126 |

\* cited by examiner

*Primary Examiner*—Jill Warden
*Assistant Examiner*—Keri Moss
(74) *Attorney, Agent, or Firm*—Dowell & Dowell, P.C.

(57) ABSTRACT

A method for measuring the concentration of isothiazolones in aqueous systems including removing sample interferences by lowering the pH of a sample collected from the aqueous system containing isothiazolones and filtering the sample, removing additional interferences by raising the pH and subsequent filtering, selectively adsorbing the isothiazolones in the sample desorbing the isothiazolones from the adsorbent, and comparing the absorbance of ultra-violet light of the desorbed sample to a standard of known concentration.

8 Claims, No Drawings

ISOTHIAZOLONE MONITORING IN AQUEOUS SYSTEMS

CROSS REFERENCE TO RELATED APPLICATIONS

This application is based on provisional application Ser. No. 60/294,556, filed on Jun. 1, 2001.

STATEMENT REGARDING FEDERALLY SPONSORED RESEARCH OR DEVELOPMENT

Not Applicable

BACKGROUND OF THE INVENTION

1. Field of the Invention

This invention relates generally to the field of monitoring of isothiazolones in aqueous systems, such as manufacturing process waters and cooling towers with concentrations of about 0.5 to 50 mg/l and more specifically to a method for the rapid measurement of isothiazolones.

2. Description of the Related Art

Isothiazolones, as defined herein, refer to substituted and unsubstituted 3-isothiazolones and mixtures having the structural formula:

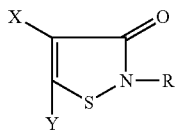

where R is hydrogen, an unsubstituted or substituted alkyl group, an unsubstituted or substituted cycloalkyl group, an unsubstituted or substituted aralkyl group, or an unsubstituted or substituted aryl group;

X and Y are independently a hydrogen atom, a halogen atom or a ($C_1$-$C_4$) alkyl group or when taken together form a substituted or unsubstituted benzene ring to give a compound of the formula:

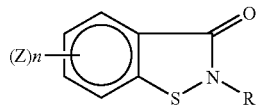

where Z is a ($C_1$-$C_4$) alkyl group, a ($C_1$-$C_4$) alkoxyl group, a cyano group, a nitrogen group, or a halogen group; and n is a integer of from zero to two.

Some of the isothiazolones present in aqueous systems may be in the form of complexed divalent salts such as magnesium or calcium.

Isothiazolones, marketed by Rohm and Haas Company and ICI, under the trademarks Kathon®, and Proxel®, respectively, are antibacterial agents or biocides which are widely used in a variety of aqueous and non-aqueous systems. For example, isothiazolones are useful as microbicides in metal working fluids, cooling tower waters, paper making waters, and textile manufacturing process waters. In addition, isothiazolones are added to a wide variety of manufactured solutions such as latex, and cosmetics and to consumer products to control the growth of microorganisms.

Attempts have been made to develop rapid, reliable and sensitive methods for determining the concentration of isothiazolones. These methods generally used sophisticated and expensive gas chromatographic, liquid chromatographic (HPLC) techniques or were colorimetric analyses directed toward field monitoring.

The HPLC methods, although accurate, are expensive to perform because they require highly trained personnel and sophisticated equipment. In addition, the analyses can take several hours to perform, especially if a column on the HPLC unit has not been prepared.

Prior field monitoring colorimetric methods have been found to be less than satisfactory because of the susceptibility of the methods to positive and negative interferences caused by additives to the aqueous systems, ionic impurities commonly found in aqueous systems, and turbidity caused by both soluble and insoluble compounds. Various additives are typically added to recirculating cooling tower water to prevent or inhibit the precipitation of hardness ions, to disperse scale, and to combat corrosion. For example, polyacrylates, phosphates, phosphonates, iron, zinc, tin and other metals are commonly found in cooling tower water as well as suspended particulate materials such as clay and silt.

However, the use of isothiazolones in some manufacturing process waters has brought new challenges in monitoring as isothiazolone concentrations must be monitored more frequently, such as hourly, by personnel having little lab experience. Further, results of monitoring must be known quickly, sometimes within minutes. In this manner, adjustments to process systems can be made immediately to prevent adverse impact to product quality.

As such, a method is needed which eliminated the eliminates potential interferences due to impurities and turbidity, can be performed quickly, can be performed by personnel of different skill levels with minimal training, and uses equipment which is readily available, reliable, and requires a minimum of maintenance.

U.S. Pat. Nos. 3,975,155 and 4,110,378 are directed to prior colorimetric determinations methods of isothiazolones in aqueous and non-aqueous systems. Partial elimination of interferences was achieved by adsorption of the isothiazolones onto an adsorbent resin, desorption of the isothiazolones, and then creation of a calorimetric reaction. Pretreatment of samples by centrifuging was required if very turbid or containing many solids, and other chemicals present could react and produce a colorimetric reaction so these chemicals had to be neutralized first. Identifying all these potential reactionary compounds could prove difficult with manufacturing waters containing many compounds.

U.S. Pat. No. 4,652,530 discloses a calorimetric determination method that also uses adsorption and desorption of the isothiazolones but onto a non-polar adsorbent. The desorbed isothiazolones are then reacted with ferric chloride and potassium ferricyanide to produce a blue color. This method also attempts to eliminate interferences through adsorption and desorption.

There were limitations with this method in that the pH of the sample for adsorption was critical. A sample pH of 10 was required as it was reported that above pH 10 the isothiazolone ring may be cleaved thereby rendering the test inaccurate and that a pH below 10 would adversely affect adsorption. In addition, this method required the use of cyanide compounds which in facilities making Food and Drug Administration (FDA) approved products would be undesirable to even have on the premises.

U.S. Pat. No. 5,094,957 discloses another calorimetric determination method that uses aromatic thiol salts added to a sample to form a colored solution. No pretreatment of the sample is performed.

Limitations with this method were that the color formed in this reaction was unstable and degraded over time. The proposed method required waiting two hours before reading the color absorbance. A two hour wait may be unacceptable for many manufacturing water systems. The method was temperature dependent and thus there was another parameter to be controlled. The method also prevented groups of samples from being measured at the sample time unless the addition of the thiol salts to each sample was timed and tracked. In addition, as with all calorimetric tests, if the sample water was highly turbid, accurate calorimetric readings were difficult to obtain.

As discussed above, current methods for the measurement of isothiazolones use:
1) expensive laboratory equipment such as HPLC, that also require highly trained personnel to both operate and maintain the equipment, and is costly and time consuming if performed by an outside laboratory;
2) calorimetric analyses that do not work when the water is turbid and contains numerous other compounds;
3) methods that take several hours to perform;
4) calorimetric methods in which the color changes over time; and
5) chemistry methods requiring the handling of hazardous materials such as cyanides, that are undesirable at many facilities to even have on the premises.

SUMMARY OF THE INVENTION

It is, therefore, an object of the present invention to provide a fast, reproducible, simple and sensitive method for monitoring low concentrations of isothiazolones in aqueous systems, without the use of HPLC, overcome the problems of interferences and high turbidity which prevent the use of the colorimetric tests, eliminate potential problems with unstable calorimetric reactions, and avoid cyanide compounds as part of the analysis.

This invention is directed toward a rapid method of measuring the isothiazolone concentration in aqueous systems using equipment that is simple to operate and maintain, can be performed by personnel with minimal training, eliminates the use of hazardous cyanide chemicals, eliminates many interferences in the samples, and measures directly the isothiazolone and not a surrogate chemical.

In particular, this invention relates to the removal of interferences in aqueous samples by processing the sample through a series of filters and membranes under conditions which allow for the passage of isothiazolone through the membrane, adsorption of the isothiazolone onto a non-polar adsorbant, desorbing of the isothiazolone and determination of the concentration by ultraviolet light adsorption.

Accordingly, several objects and advantages of the present invention are to provide:
1) a fast, reproducible, simple and sensitive method for monitoring low concentrations of isothiazolones in aqueous systems, without the use of HPLC, that can be performed lay personnel;
2) overcomes the problems of interferences and high turbidity;
3) eliminates potential problems with unstable calorimetric reactions; and
4) avoids hazardous compounds that may be undesirable to have on the manufacturing premises.

Other objects and advantages of the present invention will become apparent from the following descriptions, taken in connection with the accompanying drawings, wherein, by way of illustration and example, an embodiment of the present invention is disclosed.

It has been found that the above objectives can be realized by a novel monitoring method comprising a method for measuring the concentration of isothiazolones in aqueous systems comprising:
a. removing sample interferences by lowering the sample pH, filtering to remove solids and then filtering the sample through a media such as a filter and/or membrane which is permeable to the isothiazolones;
b. removing additional interferences by raising the pH and filtering the sample through a media such as a filter and/or membrane which is permeable to isothiazolones;
c. selectively adsorbing isothiazolones onto a non-polar adsorbent;
d. desorbing isothiazolones from the adsorbent using a solvent, and
e. determining the concentration of isothiazolones by comparing the absorbance of ultra-violet light of the desorbed sample to a standard of known concentration.

DESCRIPTION OF THE PREFERRED EMBODIMENT

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one of ordinary skills in the art to employ the present invention in virtually any appropriately detailed system, structure or manner.

The method of this invention is directed to the monitoring of isothiazolones in aqueous systems, such as manufacturing process waters and cooling towers with concentrations of about 0.5 to 50 mg/l.

The steps are detailed as follows:
1. The water sample containing the isothiazolones is first treated by adjusting the pH to at least approximately 2, with 2 being the preferred range, with an acid such as hydrochloric acid.
2. The sample is then processed through a 1.0 um filter to remove particulates and then a 0.45 um membrane to remove precipitated and hydrophobic interferences but allow permeation of the isothiazolines.
3. The sample now at pH 2, is further treated by adjusting the pH to at least approximately 9, with a range near 9 being preferred but not 10 or above, with a base such as sodium hydroxide to precipitate many other interferences.
4. The sample is then processed through a second 0.45 um membrane to remove additional interferences and allowing permeation of the isothiazolones thereby resulting in a sample relatively free of interferences.
5. The sample is then passed through a non-polar, bonded silica based adsorbent, (C-18) which has been conditioned first, onto which the isothiazolone is adsorbed.
6. The adsorbent is then rinsed with distilled water of a pH of approximately 9.
7. A solution of acetonitrile and water ranging from 40% acetonitrile and 60% distilled water, to 60% acetonitrile and 40% distilled water is used to elute or de-sorb the isothiazolones from the adsorbent.
8. The concentration of isothiazolones in the elutant is then determined by comparing the absorbance of the elutant in a spectrophotometer at a wavelength of approximately 276 nm to the absorbance of known standards.

9. Conditioning of the non-polar silica based adsorbent involves washing it with 100% acetonitrile followed by a rinse of distilled water whose pH has been adjusted to 9 with hydrochloric acid or sodium hydroxide. This conditioning removes many interferences from the adsorbent prior to its use.

EXAMPLE

The following is a non-limiting example of the invention.

Notes:
A. All syringes used are glass with Teflon plungers.
B. A commercially available cartridge containing the C-18 non-polar bonded silica from Waters Corporation is used for the adsorption of the isothiazolones. This cartridge contained approximately 320 mg of silica and can be affixed to a syringe.
C. The cartridge is conditioned prior to use by passing 10 ml of 100% acetonitrile through it drop wise followed by 10 ml of pH 9 distilled water drop wise.

1. A 30 ml sample of process manufacturing water is collected and 5 N hydrochloric acid is added drop wise to the sample until the pH is lowered to 2.
2. The sample is then filtered using a syringe affixed with a 1 um glass fiber syringe filter to which has been affixed a 0.45 um membrane syringe filter.
3. The pH of the filtered sample is then raised to 9 by adding 0.5 N sodium hydroxide drop wise.
4. The sample now at pH 9 is filtered using a syringe through another 0.45 um membrane syringe filter.
5. A 5 ml aliquot of the filtered sample now at pH 9 is collected in a syringe, the cartridge is affixed to the syringe and the sample is passed drop wise through the adsorbent cartridge.
6. The cartridge is then rinsed by using a syringe to pass 10 ml of pH 9 distilled water drop wise through the cartridge.
7. The isothiazolones are then desorbed from the adsorbent by using a syringe to pass a 10 ml solution (elutent) of 40% acetonitrile and 60% distilled water drop wise through the cartridge.
8. The absorbance of the elutent is then measured in a spectrophotometer at 276 nm and compared to the absorbance of known standards.

Table 1 shows data from Kathon standards processed using the above method. The standards had a correlation coefficient of 1, demonstrating good correlation between concentration and absorbance over a wide concentration range.

TABLE 1

| Isothiazolone Conc, mg/l | Absorbance at 276 nm |
|---|---|
| 0 | 0.0047 |
| 1 | 0.0257 |
| 3 | 0.0684 |
| 5 | 0.1117 |
| 50 | 1.1057 |

Correlation Coefficient = 1

Table 2 shows the need to both lower and raise the pH of process water samples to obtain accurate results. In this case the sample was analyzed by the method described above and by two variations. In the first variation, steps of raising the pH to 9 and then passing through the membrane a second time were omitted. In the second variation, steps of lowering the sample pH to 2 and filtering through the membrane were omitted. These two variations are compared to the full procedure and to results by HPLC. These results demonstrate that erroneously high readings would be obtained unless both pH adjustment steps are included in the analysis for certain process waters.

TABLE 2

| Variation | Isothiazolone Concentration, mg/l |
|---|---|
| 1 - Filtered only at pH 2 | 4.4 |
| 2 - Filtered only at pH 9 | 5.50 |
| 3 - Normal procedure | 3.44 |
| HPLC | 3.43 |

The isothiazolone concentrations estimated using this invention are presented in Table 3 along with a comparison to the same samples analyzed by High Performance Liquid Chromatography (HPLC) These water samples were treated with Kathon and were extremely turbid and contained many dissolved compounds. Each sample took approximately 15 minutes to analyze using this method and there was a correlation coefficient of 0.976 with the HPLC results thus showing good agreement with the accuracy of HPLC.

TABLE 3

| Sample Number | Estimated Concentration, mg/l | |
|---|---|---|
| | HPLC | Rapid UV Analysis |
| 1 | 3.04 | 2.97 |
| 2 | 2.95 | 2.86 |
| 3 | 5.65 | 5.64 |
| 4 | 4.67 | 4.49 |
| 5 | 3.81 | 4.09 |
| 6 | 4.39 | 4.36 |
| 7 | 4.47 | 4.57 |

Correlation Coefficient = 0.976

Table 4 shows data from a sample demonstrating the stability of the absorbance readings over time. One sample was processed by the above method and the absorbance read at 0, 6, and 12 hours.

TABLE 4

| Time, hours | Absorbance at 276 nm | % Delta From 0 Hours |
|---|---|---|
| 0 | 0.0902 | 0 |
| 6 | 0.0885 | 1.88 |
| 12 | 0.0895 | 0.78 |

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. A method for measuring the concentration of isothiazolones in aqueous systems including the steps of:
   a. removing sample interferences by lowering a pH to about 2 of a sample collected from the aqueous system containing isothiazolones, and thereafter, filtering the sample;

b. removing additional interferences by raising the pH of the sample to approximately 9, and thereafter, filtering the sample;

c. selectively adsorbing said isothiazolones in the sample onto a non-polar adsorbent;

d. desorbing said isothiazolones from said adsorbent, and e. determining the concentration of said isothiazolones by comparing absorbance of ultra-violet light of the desorbed sample to a standard of known concentration.

2. The method of claim 1 where the isothiazolone concentration in the aqueous systems ranges from approximately 0.5 to 50 mg/l.

3. The method of claim 1 where the non-polar adsorbent includes bonded phase silica gel.

4. The method of claim 1 where a solution ranging from 40% acetonitrile and 60% distilled water, to 60% acetonitrile and 40% distilled water is used to desorb the adsorbed isothiazolones.

5. The method of claim 1 where the adsorbent is conditioned before adsorbing the isothiazolones by rinsing the adsorbent with acetonitrile followed by deionized water of a pH of approximately 9.

6. The method of claim 1 wherein, in step a, the filtering is through a filter and then a membrane.

7. The method of claim 6 wherein, in step b, the filtering is through a membrane.

8. A method for determining concentrations of isothiazolones in an aqueous system of from about 0.5 to 50 mg/l comprising:

a. removing sample interferences by lowering the a pH to 2 of a sample collected from the aqueous system containing isothiazolones and, thereafter, filtering the sample through a 1 micron filter of approximately 1 micron followed by a membrane of approximately 0.45 micron;

b. removing additional interferences by raising the pH to approximately 9 and, thereafter, filtering the sample through a membrane of approximately 0.45 micron;

c. selectively adsorbing said isothiazolones from the treated sample onto a conditioned nonpolar, bonded phase, silica gel adsorbent;

desorbing said isothiazolones from the adsorbent using a solution of acetonitrile and deionized water; and the concentration of said desorbed isothiazolones by determining comparing absorbance of ultra-violet light at approximately 276 nanometers of the desorbed sample to the absorbance of a standard of known isothiazolone concentration.

* * * * *